United States Patent
Roopchand

[11] Patent Number: 5,941,246
[45] Date of Patent: Aug. 24, 1999

[54] ENDOTRACHEAL TUBE SUPPORT

[76] Inventor: Roland Roopchand, 100 Rose Drive, Elizabeth Gardens, St. Joseph, Trinidad/Tobago

[21] Appl. No.: 08/962,241

[22] Filed: Oct. 31, 1997

[51] Int. Cl.[6] .............................. A61M 16/00; A62B 9/06
[52] U.S. Cl. ................ 128/207.14; 128/859; 128/861; D24/128
[58] Field of Search ......................... 128/200.26, 201.26, 128/206.29, 207.14, 207.17, 911, 912, DIG. 26, 848, 859, 860, 861; D24/110, 127, 128, 156, 176, 180, 181, 190, 191

[56] References Cited

U.S. PATENT DOCUMENTS

| | | | |
|---|---|---|---|
| 803,475 | 10/1905 | Dennis | 601/164 |
| 4,261,354 | 4/1981 | Nelson | 128/203.23 |
| 4,275,725 | 6/1981 | Nelson | 128/207.14 |
| 4,289,127 | 9/1981 | Nelson | 128/207.14 |
| 4,329,984 | 5/1982 | Kervin | 128/207.14 |
| 4,425,911 | 1/1984 | Luomanen et al. | 128/200.26 |
| 4,495,945 | 1/1985 | Liegner | 128/200.26 |
| 4,896,667 | 1/1990 | Magnuson et al. | 128/207.14 |
| 5,195,513 | 3/1993 | Sinko et al. | 128/200.26 |
| 5,386,821 | 2/1995 | Poterack | 128/200.26 |
| 5,626,128 | 5/1997 | Bradley et al. | 128/200.26 |
| 5,638,811 | 6/1997 | David | 128/207.14 |
| 5,829,430 | 11/1998 | Islava | 128/200.26 |
| 5,862,801 | 1/1999 | Wells | 128/200.26 |
| 5,865,170 | 2/1999 | Moles | 128/201.26 |
| 5,884,625 | 3/1999 | Hart | 128/207.14 |

*Primary Examiner*—John G. Weiss
*Assistant Examiner*—Joseph F. Weiss, Jr.
*Attorney, Agent, or Firm*—Rogers & Scott

[57] ABSTRACT

An endotracheal tube support includes a mouthguard and a tube clip secured thereto. The mouthguard has a generally U-shape with a bottom wall and opposed side walls extending upwardly from opposite edges thereof to enable the mouthguard to be positioned over a patient's upper teeth or gum. The clip is of resilient material and has an elongated cylindrical shape with a longitudinally extending opening extending along the entire length thereof to enable an endotracheal tube to be snapped therethrough. The clip is secured beneath the mouthguard on one side thereof by a fastening device extending from the bottom wall of the mouthguard to a position on the clip substantially opposite the longitudinally extending opening therein.

5 Claims, 1 Drawing Sheet

ENDOTRACHEAL TUBE SUPPORT

FIELD OF THE INVENTION

This invention relates to endotracheal tube supports which are positionable in the mouth of a patient to properly position the tube therein.

BACKGROUND OF THE INVENTION

An endotracheal tube support is described in U.S. Pat. No. 5,626,128 (Bradley et al.) issued May 6, 1997 and is stated to be well-adapted for patients suffering from facial burns, dermatitis or cleft palate syndrome.

It is an object of the present invention to provide an improved endotracheal tube support which is suitable for more general use during routine general anesthesia.

SUMMARY OF THE INVENTION

According to the present invention, an endotracheal tube support includes a mouthguard and a tube clip secured thereto, the mouthguard having a generally U-shape with a bottom wall and opposed side wall extending upwardly from opposite edges thereof to enable the mouthguard to be positioned over a patient's upper teeth or gum, and the clip being of resilient material and having an elongated cylindrical shape with a longitudinally extending opening extending along the entire length thereof to enable an endotracheal tube to be snapped therethrough, the clip being secured beneath the mouthguard on one side thereof by a fastening device extending from the bottom wall of the mouthguard to a portion of the clip substantially opposite the longitudinally extending opening therein.

An endotracheal tube support in accordance with the present invention is especially useful during routine general anaesthesia because it is simple and easy to apply. It also provides improved access to the oral cavity for suctioning. The present invention also enables tube support to be inexpensive and disposable so that such a tube support can be supplied with every endotracheal tube.

The mouthguard may be an integral rubber molding, the clip may be made of a resilient silicone material, and the fastening device may comprise a pair of rivets.

BRIEF DESCRIPTION OF THE DRAWINGS

One embodiment of the invention will now be described, by way of example, with reference to the accompanying drawings, of which.

DETAILED DESCRIPTION OF PREFERRED EMBODIMENT

Figure 1:
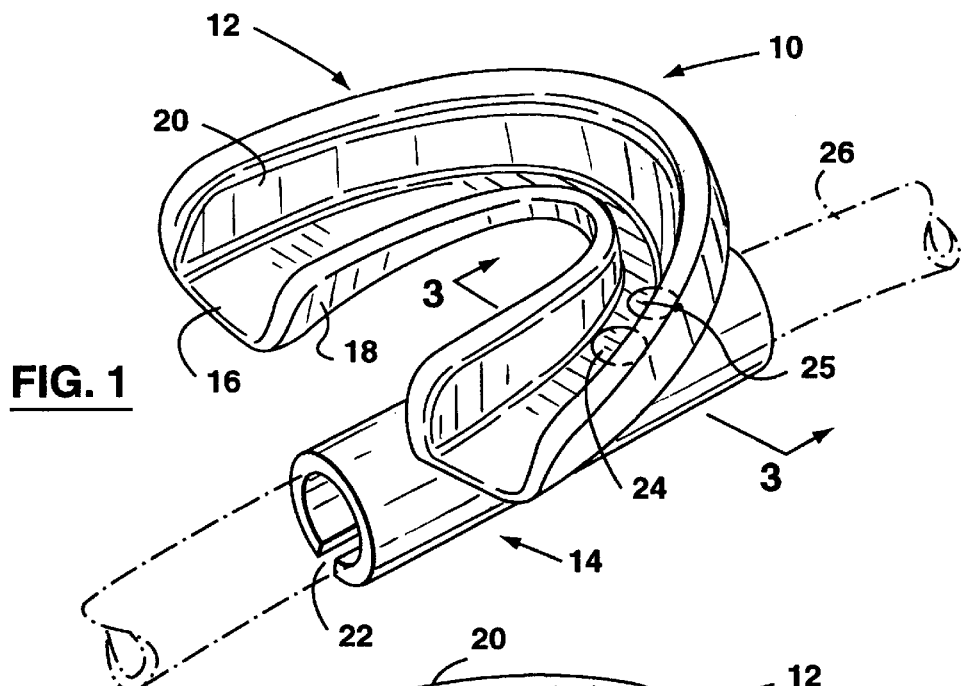
FIG. 1 is a perspective view from above of an endotracheal tube support in accordance with the invention mounted on an endotracheal tube.
Figure 2:
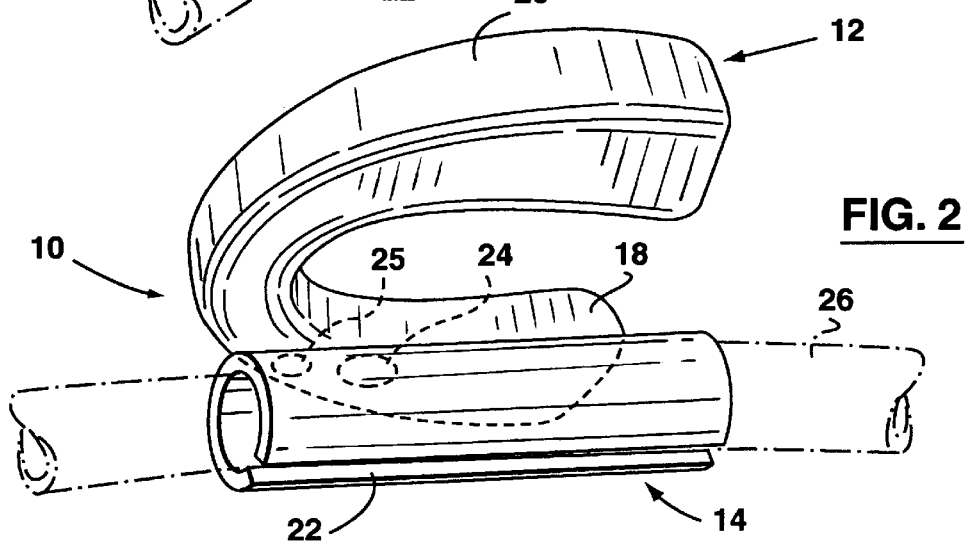
FIG. 2 is a similar view but from below.
Figure 3:
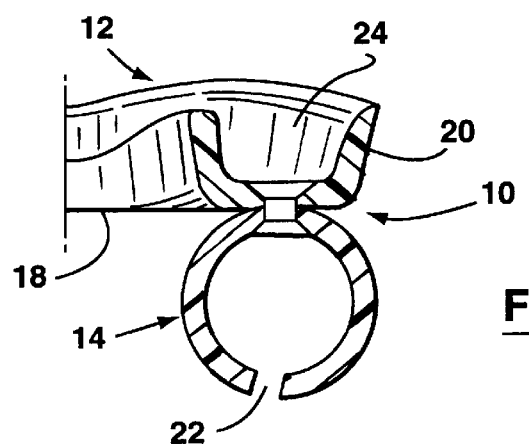
FIG. 3 is a sectional view of the tube support taken along the line 3—3 of FIG. 1.

Referring to the drawings, an endotracheal tube support 10 in accordance with one embodiment of the invention includes a mouthguard 12 and a tube clip 14 secured thereto. The mouthguard 12 is an integral rubber molding and has a generally U-shape with a bottom wall 16 and opposed side walls 18, 20 extending upwardly from opposite edges thereof. The clip 14 is made of resilient silicone material, and has an elongated cylindrical shape with a longitudinal extending opening 22 extending along the entire length thereof.

The clip 14 is secured beneath the mouthguard 12 on one side thereof by a pair of plastic rivets 24, 25 which pass through the bottom wall 16 of the mouthguard 12 and through a portion of the clip 14 substantially opposite the longitudinal extending opening 22 therein.

The tube support 10 can readily be secured to an endotracheal tube 26 (shown in dotted outline) by simply snapping the tube 26 through the longitudinal extending opening 22 into the clip 14. The endotracheal tube 26 is commonly made of a plastic material (such as PVC) which has a natural adhesiveness with the silicone material of which the clip 14 is made. During insertion of the endotracheal tube 26 into a patient, the mouthguard 12 is positioned over the patient's upper teeth or gum.

A person skilled in the art will readily understand the advantages of the present invention from the foregoing description of the preferred embodiment. The positioning of the clip 14 on one side of the mouthguard 12 provides good access to the patient's mouth, the clip 14 is easily secured to the endotracheal tube 26, and the tube 26 is supported along the full length of the clip 14, thereby minimizing instability of the tube 26 at this location. Also, the tube support 10 is inexpensive, disposable and can be provided with every endotracheal tube 26. Additionally, no adhesive is required to secure the mouthguard 12 in the patient's mouth.

Other embodiments of the invention will also be readily apparent to a person skilled in the art, the scope of the invention being defined in the appended claims.

I claim:

1. An endotracheal tube support including a mouthguard and a tube clip secured thereto, the mouthguard having a generally U-shape with a bottom wall and opposed side walls extending upwardly from opposite edges thereof to enable the mouthguard to be positioned over a patient's upper teeth or gum, and the clip being of resilient material and having an elongated cylindrical shape with a longitudinally extending opening extending along the entire length thereof to enable an endotracheal tube to be snapped therethrough, the clip being secured beneath the mouthguard on one side thereof by a fastening device extending from the bottom wall of the mouthguard to a position on the clip substantially opposite the longitudinally extending opening therein.

2. An endotracheal tube support according to claim 1 wherein the mouthguard is an integral rubber molding.

3. An endotracheal tube support according to claim 1 wherein the clip is made of a resilient silicone material.

4. An endotracheal tube support according to claim 1 wherein the fastening device comprises a pair of rivets.

5. An endotracheal tube support according to claim 1 wherein the mouthguard is an integral rubber molding, the clip is made of a resilient silicone material and the fastening device comprises a pair of rivets.

* * * * *